(12) United States Patent
Chang

(10) Patent No.: US 6,974,692 B2
(45) Date of Patent: Dec. 13, 2005

(54) QUANTITATIVE CELL-COUNTING SLIDE FOR SIMULTANEOUSLY SATISFYING MULTIPLE VOLUMETRIC UNITS

(76) Inventor: Mao-Kuei Chang, 1st Floor, No. 24, Lane 78, Hsin-Ai Road, Nei-Hu District, Taipei (TW) 114

( * ) Notice: Subject to any disclaimer, the term of this patent is extended or adjusted under 35 U.S.C. 154(b) by 0 days.

(21) Appl. No.: 10/794,238

(22) Filed: Mar. 5, 2004

(65) Prior Publication Data

US 2004/0180397 A1   Sep. 16, 2004

(30) Foreign Application Priority Data

Mar. 14, 2003  (TW) .............................. 92203939 U

(51) Int. Cl.[7] .............................................. C12M 1/34
(52) U.S. Cl. ............................... 435/288.3; 435/288.4; 359/396; 359/397; 359/398; 356/244; 356/246; 422/102
(58) Field of Search ................................ 359/396, 397, 359/398; 356/244, 246; 422/102; 435/288.3, 435/288.4

(56) References Cited

U.S. PATENT DOCUMENTS

| | | | | |
|---|---|---|---|---|
| 5,128,802 A | * | 7/1992 | Mitchell | ...................... 359/397 |
| 6,594,077 B2 | * | 7/2003 | Chiarin et al. | .............. 359/397 |

* cited by examiner

Primary Examiner—David Redding

(57) ABSTRACT

A quantitative cell-counting slide includes a plurality of counting chambers juxtapositionally formed in the slide; each counting chamber including a first counting portion consisting of a plurality of miniature grids of which each miniature grid may be formed to have a volume of 0.01 micro-liter for counting any kind of cells, and a second counting portion formed on a platform and consisting of a plurality of HPF (High Power Field) volumetric grids each formed to have a quantitative volume of 0.0083 micro-liter generally equal to one HPF volume adapted for cell counting used in urinary sediment microscopic examination.

6 Claims, 7 Drawing Sheets

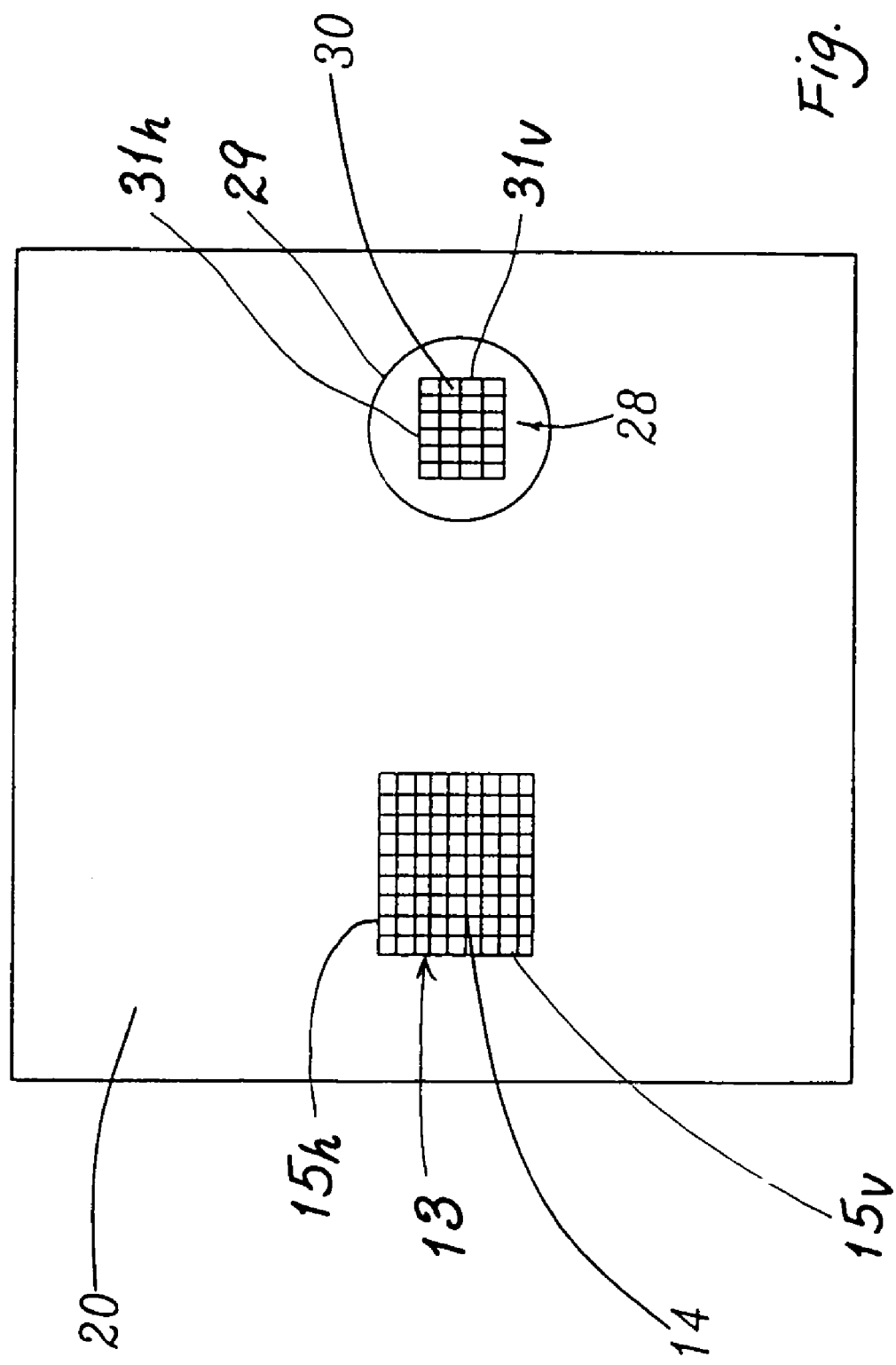

QUANTITATIVE CELL-COUNTING SLIDE FOR SIMULTANEOUSLY SATISFYING MULTIPLE VOLUMETRIC UNITS

BACKGROUND OF THE INVENTION

Conventional glass slide has been replaced by plastic slide for microscopically counting the cells more precisely.

U.S. Pat. No. 5,021,294 to Karasawa et al. disclosed a plastic slide for microscope including at least one surface of the slide rendered hydrophilic so that a staining solution used in microscopic examination may not be repelled.

However, the conventional plastic slide does not disclose the method and device for simultaneously counting cells in different volumetric units on the same slide.

SUMMARY OF THE INVENTION

The object of the present invention is to provide a quantitative cell-counting slide including a plurality of counting chambers juxtapositionally formed in the slide; each counting chamber including a first counting portion consisting of a plurality of miniature grids of which each miniature grid may be formed to have a volume of 0.01 micro-liter for counting any kind of cells, and a second counting portion formed on a platform and consisting of a plurality of HPF (High Power Field) volumetric grids each formed to have a quantitative volume of 0.0083 micro-liter generally equal to one HPF volume adapted for cell counting used in urinary sediment microscopic examination.

BRIEF DESCRIPTION OF THE DRAWINGS

FIG. 7 is a top-view illustration of the first and second counting portions of the present invention.

DETAILED DESCRIPTION

Figure 1:
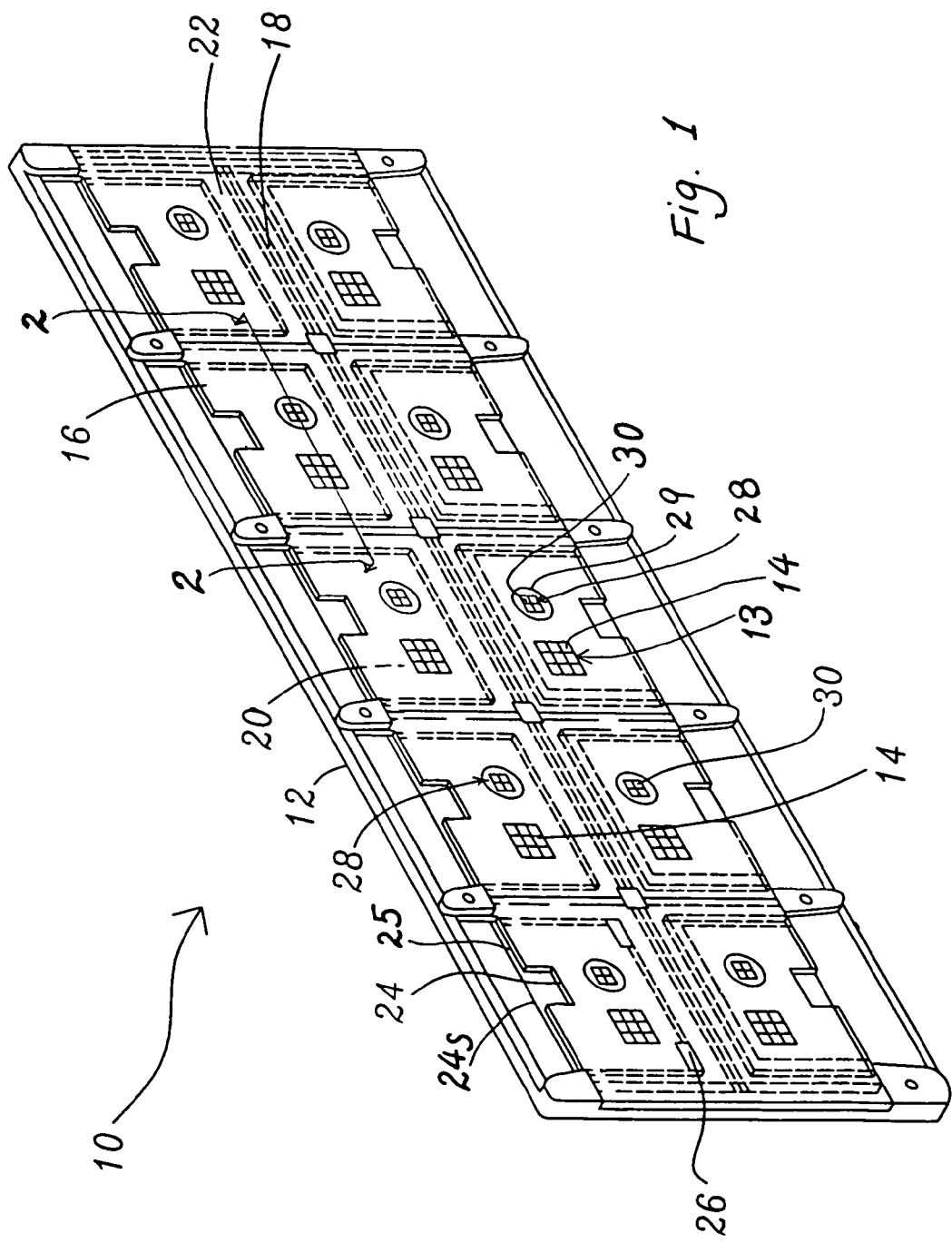
FIG. 1 is a perspective view of the present invention.

As shown in the drawing figures, the quantitative cell-counting slide 10 of the present invention comprises: a bottom plate 12, a plurality of counting chambers 20 (such as ten chambers 20 as illustrated in the accompanying drawing figures), and a cover plate 16 covering the chambers 20 and the bottom plate 12; each said counting chamber 20 including a first counting portion 13 for counting any kind of cells thereon, and a second counting portion 28 for counting special cells such as cells in urinary sediment specimen. All elements of the slide 10 should be made of transparent materials for optical microscopic examination.

Each counting chamber 20 includes: a base 12b protruded upwardly from the bottom plate 12, at least a side groove 22 disposed around the base 12b and recessed downwardly from the base 12b to form as a drain "trench" for draining the sample fluid thereinto, at least a partition wall 18 circumferentially confining the side groove 22 and confining each counting chamber 20 for partitioning two neighboring counting chambers 20 for precluding the leakage or flow of sample fluid among the counting chambers 20.

Each counting chamber 20 includes a filling port 24 notched in an opening end portion 25 formed in an outer portion of the counting chamber 20 for filling the sample fluid L into the chamber 20 by a pipet P, having a sloping access portion 24s adjacent to the filling port 24 for helping a smooth loading of sample fluid into the chamber 20. The sample fluid will fill the chamber 20 for counting cells in the first and second counting portions 13, 28.

Two or plural venting ports 26 are formed in an inner portion of the counting chamber 20 between the base 12b and the cover 16 for venting air for quickly filling sample fluid into the counting chamber 20 without forming air pocket.

Figure 3:
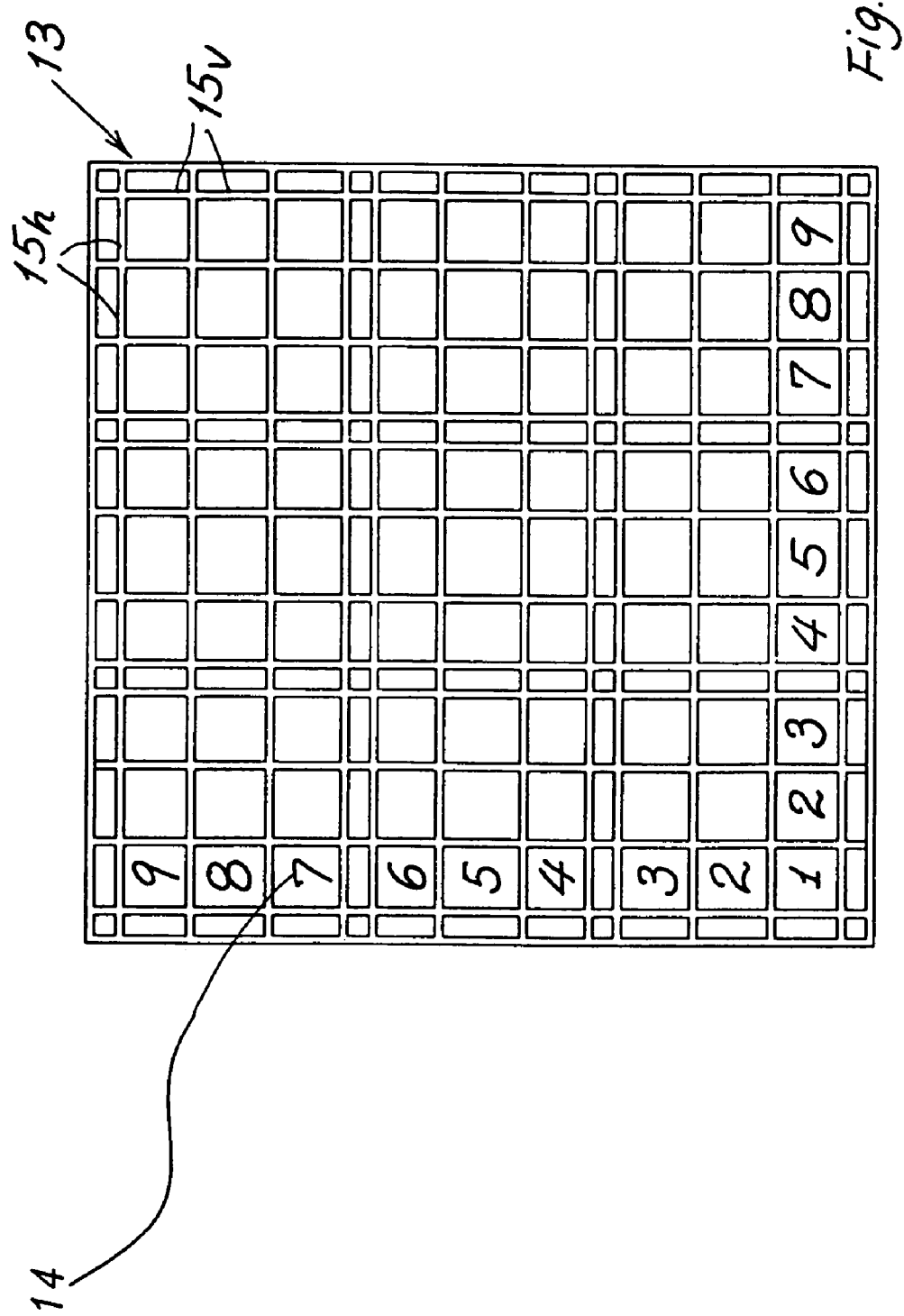
FIG. 3 is a top view of the first counting portion of the present invention.
Figure 4:
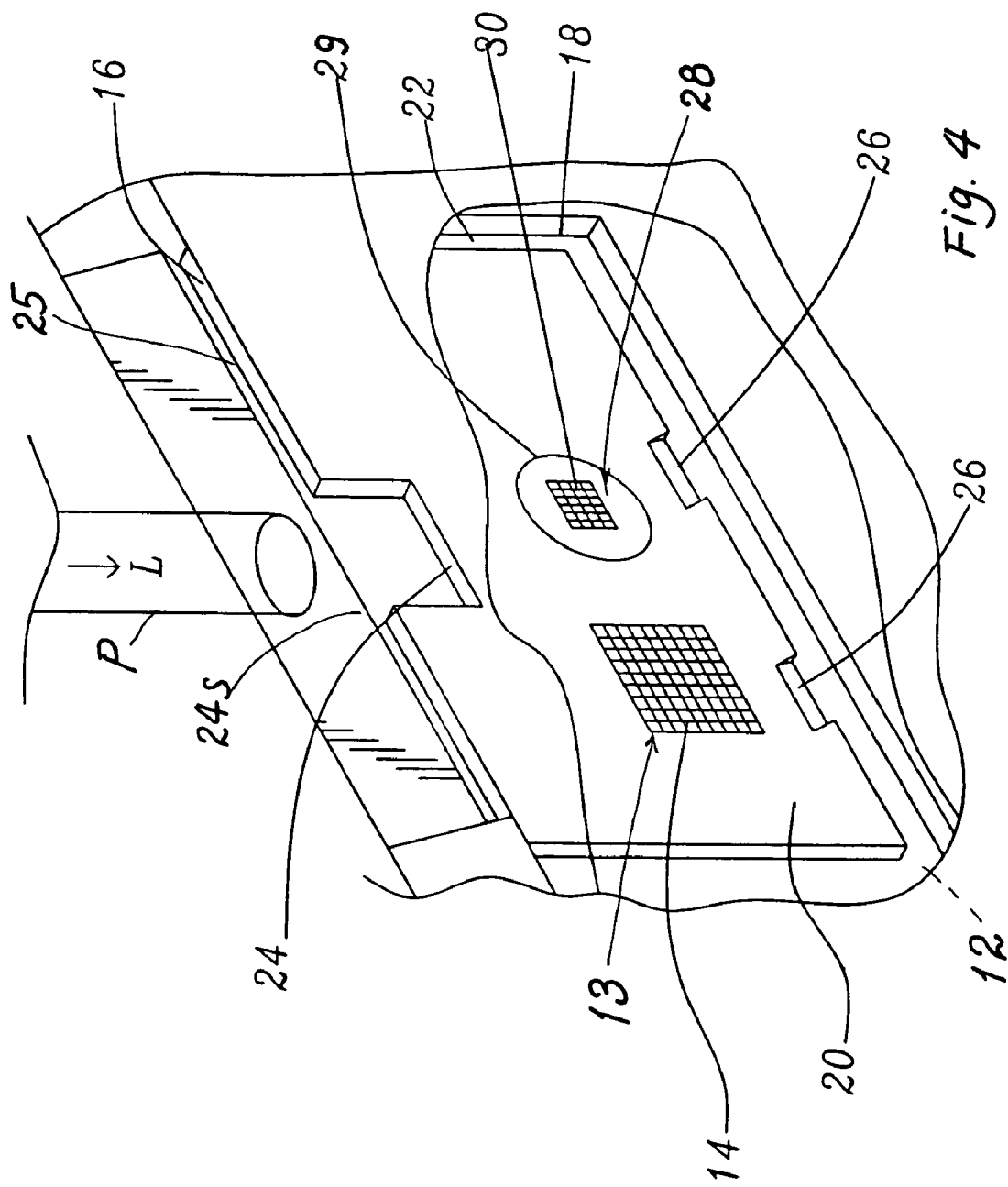
FIG. 4 is a partial perspective view of each counting chamber of the present invention.

The first counting portion 13 is formed on the base 12b protruded upwardly from the bottom plate 12, including a plurality of longitudinal (or vertical) side walls 15v and a plurality of latitudinal (or horizontal) side walls 15h with each side wall 15v interlaced with each side wall 15h to form a plurality of miniature (or first) grids 14 of which each grid 14 which may have a size of 0.33 mm length×0.33 mm width×0.1 mm depth, corresponding to a volume of 0.01 micro-liter per miniature grid 14. As shown in FIG. 3, there are 81 grids (9×9=81) formed in the first counting portion 13. However, the size of each grid 14 is not limited in the present invention. The total area of the first counting portion 13 may be 3 mm×3 mm=9 mm². The depth of the counting chamber 20 at the first counting portion 13 is 0.1 mm. Comparatively, the internal volume of the counting chamber is 8.1 micro-liters, based on a dimension of 9 mm length×9 mm width×0.1 mm depth.

The second counting portion 28 is formed in the counting chamber 20 juxtapositional to the first counting portion 13. The second counting portion 28 is formed as a circular shape to be distinguished from the square-shaped first counting portion 13 of the present invention. However, their shapes are not limited in this invention.

Figure 2:
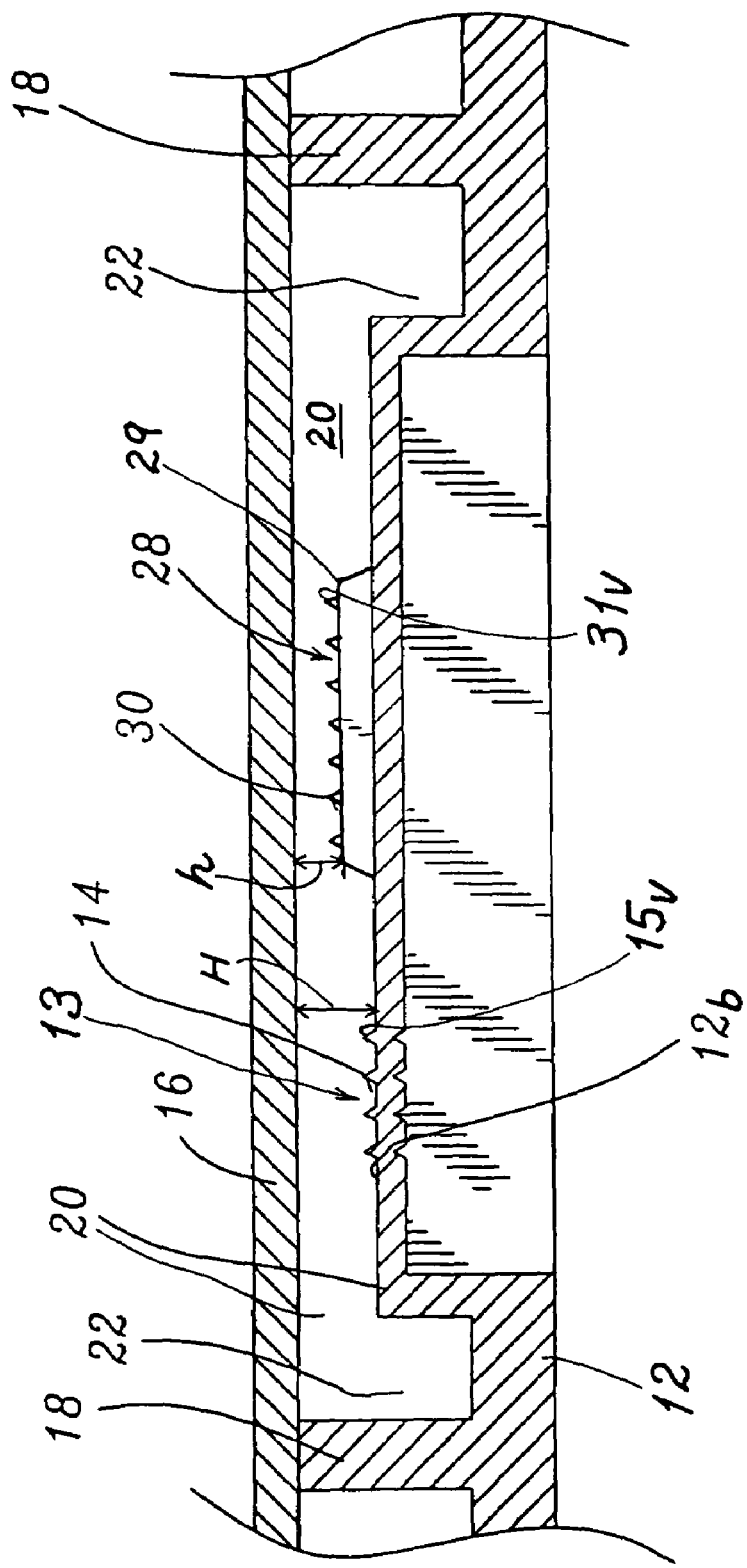
FIG. 2 is a partial sectional drawing as taken from 2—2 direction of FIG. 1
Figure 5:
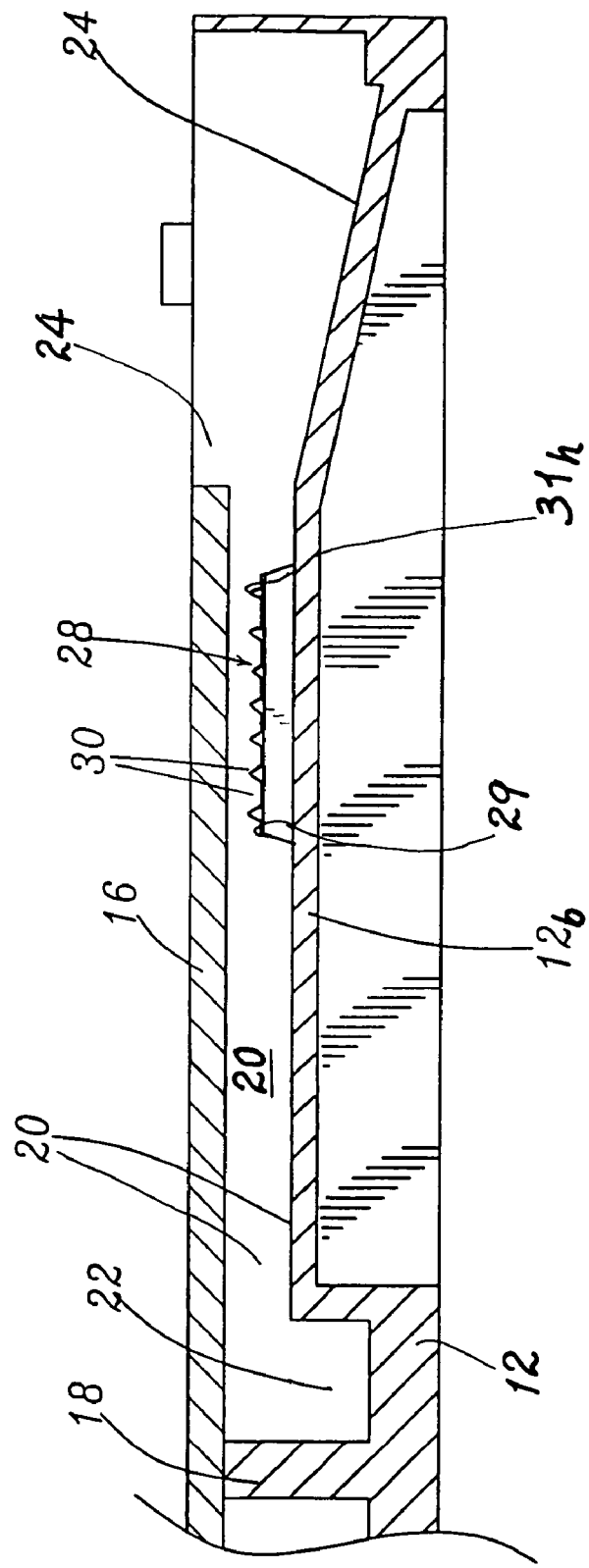
FIG. 5 is a longitudinal sectional drawing of the counting chamber of the present invention.
Figure 6:
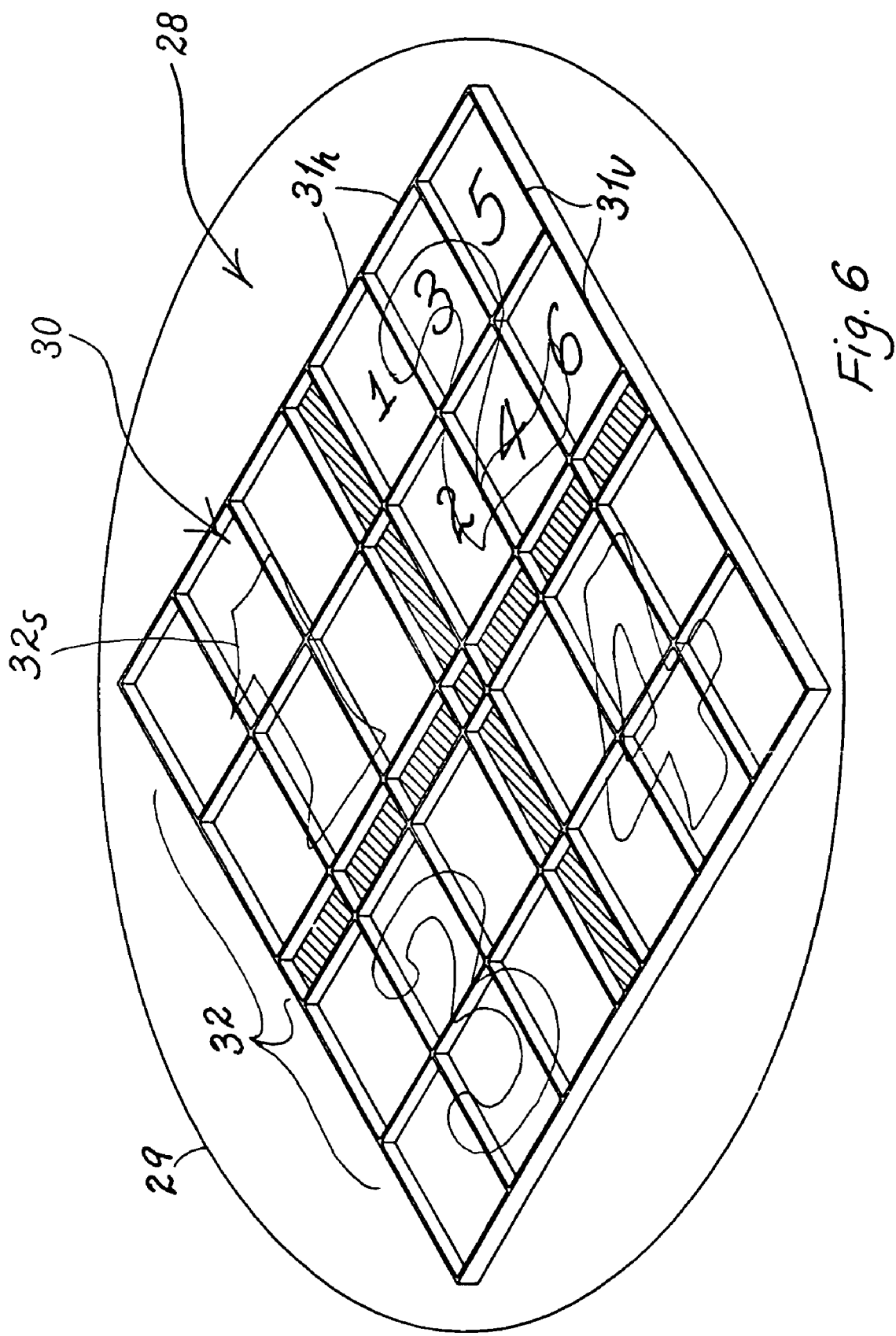
FIG. 6 is a perspective view of the second counting portion of the present invention.

The second counting portion 28, especially as shown in FIGS. 2, 5 and 6, includes: a circular-shaped platform 29 (or formed as other geometrical shapes) protruding upwardly from the base 12b to define a depth of 0.05 mm in the counting chamber 20 (the depth "h" of 0.05 mm as set between the platform 29 and the inside surface of the cover 16 when filling the sample fluid in the counting chamber 20, which depth "h" is one half of the full depth H of the base 12b), a plurality of HPF (High Power Field) volumetric grids (or second grids) 30 formed on the platform 29, each HPF volumetric grid 30 having a volume of 0.0083 micro-liter which is a cell-counting unit adapted for urinary sediment microscopic examination. The size of the platform 29 may be 3.5 mm diameter having a depth of 50 micro-meter.

For forming the HPF volumetric grids 30, a plurality of longitudinal (or vertical) side walls 31v and a plurality of latitudinal (or horizontal) side walls 31h are interlaced to form a square lattice 32 within the circular platform 29, consisting of a plurality of HPF volumetric grids 30 each formed as a rectangular shape.

As shown in FIG. 6, the square lattice 32 may be divided into four sub-lattices 32s each consisting of six HPF volumetric grids 30. In practical measurement, each sub-lattice 32s has a dimension of 1 mm length×1 mm width×0.05 mm depth, which is equal to 0.05 micro-liter. Therefore, each HPF volumetric grid 30 has a volume of 0.0083 micro-liter which is obtained by the following formula: 0.05 micro-liter÷6=0.0083 micro-liter.

Each HPF volumetric grid 30 has a volume of 0.0083 micro-liter which is fallen within the volume range ranging from 0.008 micro-liter through 0.0098 micro-liter of the so-called HPF volume designated as a cell-counting unit for an urinary sediment microscopical examination. Therefore, the cell number per HPF for an urinary sediment examination may be directly immediately obtained from the grids 30 when examined by microscope. It is not necessary to multiply a factor to the counting result of urinary sediment test by a conventional slide due to different concentration ratio (or times).

Accordingly, the present invention may be provided for counting cells, especially for urinary sediment examination, directly precisely on the second counting portion 28. Since the depth (h) of each HPF grid 30 is one-half of the depth (H) of the miniature grid 14, the cell number, if being increased in a specimen, can be simultaneously checked in the first counting portion 13 and in the second counting portion 28 for double check and precise calibration. This is because the depth (h) in second counting portion 28 is shallower (one half) than that depth (H) of the first counting portion 13, to eliminate the overlapping of cells in a deep grid in order to clearly observe and count the cell number more precisely (since the cell number per microscopic power field in the second grid 30 will become smaller).

The present invention has the following advantages superior to the prior arts:
1. A first counting portion 13 and a second counting portion 28 may be simultaneously used for double checking and reliable calibration for counting cells.
2. A special examination such as for counting cells in an urinary sediment can be directly done in the second counting portion 28 which is shallower in depth than that of the first counting portion 13 to thereby prevent from overlapping of cells or bacteria in the specimen solution for a clearer microscopic observation and more precise cell-counting.
3. The second counting portion 28 includes a plurality of HPF volumetric grids 30 each grid 30 having a HPF (High Power Field) volume for a direct cell-counting per HPF, thereby eliminating the conversion by multiplying a factor to a measured data for preventing error as occurred in the conventional method.
4. Different volumetric units are provided for respective cell-counting purposes. The first counting portion 13 may be provided for counting any kind of cells, while the second counting portion 15 may be provided for counting cells for special examination such as urinary sediment test, thereby increasing the utility and commercial value of the present invention.

The present invention may be modified without departing from the spirit and scope of the present invention

I claim:

1. A cell-counting slide comprising:
a plurality of counting chambers juxtapositionally formed in a transparent slide; each said counting chamber including a first counting portion formed in said counting chamber and consisting of a plurality of first grids each said first grid having a first depth in said counting chamber for counting cells in said first grids of said first counting portion, and a second counting portion formed in said counting chamber and juxtapositoned to said first counting portion;

said second counting portion consisting of a plurality of second grids, each said second grid having a second depth in said counting chamber being shallower than the first depth of said first grid, whereby upon counting of cells in said second grid of said second counting portion in a shallower depth in said counting chamber than that of said first grid of said first counting portion, a clearer microscopic examination than that of the first grid will be obtained.

2. A cell-counting slide according to claim 1, wherein each said counting chamber includes: a base protruded upwardly from a bottom plate of said counting chamber, at least a side groove disposed around the base and recessed downwardly from the base for draining a sample fluid filled into the counting chamber, and at least a partition wall circumferentially confining the side groove and confining each said counting chamber within said partition wall for partitioning two neighboring counting chambers.

3. A cell-counting slide according to claim 2, wherein said counting chamber includes a filling port notched in an opening end portion formed in an outer portion of the counting chamber for filling sample fluid into the counting chamber, having a sloping access portion adjacent to the filling port for helping a smooth loading of the sample fluid into the counting chamber, and a plurality of venting ports formed in an inner portion of the counting chamber between the base and a cover covering said counting chambers and said bottom plate.

4. A cell-counting slide according to claim 1, wherein said second counting portion includes: a platform protruding upwardly from a base in said counting chamber, said second grid formed on said platform being a HPF (High Power Field) volumetric grid, each said HPF volumetric grid having a volume of 0.0083 micro-liter which is a cell-counting unit adapted for urinary sediment microscopic examination.

5. A cell-counting slide according to claim 4, wherein said plurality of HPF volumetric grids are formed by a plurality of longitudinal (or vertical) side walls interlaced with a plurality of latitudinal (or horizontal) side walls to form a square lattice consisting of said HPF volumetric grids within the platform.

6. A cell-counting slide according to claim 5, wherein said square lattice is divided into four sub-lattices each consisting of six said HPF volumetric grids.

* * * * *